US00PP18047P2

(12) United States Plant Patent
Schoenmakers

(10) Patent No.: US PP18,047 P2
(45) Date of Patent: Sep. 18, 2007

(54) ***FITTONIA* PLANT NAMED 'RED STAR'**

(50) Latin Name: *Fittonia verschaffeltii*
Varietal Denomination: Red Star

(75) Inventor: Kees Schoenmakers, Haaren (NL)

(73) Assignee: Schoenmakers Tropische Potcultures, Haaren (NL)

( * ) Notice: Subject to any disclaimer, the term of this patent is extended or adjusted under 35 U.S.C. 154(b) by 7 days.

(21) Appl. No.: 11/287,062

(22) Filed: Nov. 25, 2005

(51) Int. Cl.
*A01H 5/00* (2006.01)

(52) U.S. Cl. ..... Plt./373

(58) Field of Classification Search ..... Plt./373, Plt./263
See application file for complete search history.

(56) References Cited

PUBLICATIONS

GTITM UPOVROM Citation for 'Red Star' as per NL PBR FTN0018; Aug. 29, 2002.*
GTITM UPOVROM Citation for 'Red Star' as per NL PBR FTN0025; Aug. 9, 2004.*

* cited by examiner

*Primary Examiner*—Kent Bell

(57) ABSTRACT

A new cultivar of *Fittonia* plant named 'Red Star' that is characterized by small pink to red leaves with green wavy margins and spots.

1 Drawing Sheet

Botanical classification: *Fittonia verschaffeltii.*
Variety denomination: 'Red Star'.

BACKGROUND OF THE INVENTION

The present invention relates to a new and distinct cultivar of *Fittonia* plant botanically known as *Fittonia verschaffeltii* and hereinafter referred to by the cultivar name 'Red Star'.

The new cultivar was discovered by the inventor in a cultivated area of Haaren, The Netherlands in February 2003. 'Red Star' was discovered as a naturally occurring whole plant mutation of *Fittonia* 'Josan' (not patented).

Asexual reproduction by terminal cuttings of the new cultivar 'Red Star' was first done in June 2003 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'Red Star'.

1. *Fittonia* 'Red Star' exhibits small leaves.
2. *Fittonia* 'Red Star' exhibits pink to red leaves with green margins and spots.
3. *Fittonia* 'Red Star' exhibits wavy leaf margins.

The closest comparison cultivar is *Fittonia* 'Pink Star' (U.S. Plant patent application Ser. No. 11/287,064). The new cultivar *Fittonia* 'Red Star' is distinguishable from *Fittonia* 'Pink Star' by the following characteristics:

1. 'Red Star' exhibits pink to red leaves with green margins and spots. The leaves of 'Pink Star' are pink with green margins and spots.

The new cultivar 'Red Star' is distinguishable from the parent plant 'Josan' by the following characteristics:

1. 'Red Star' is more compact than 'Josan'.
2. 'Red Star' has leaves that are narrower than those of 'Josan'.

BRIEF DESCRIPTION OF THE DRAWING

The accompanying photograph illustrates the distinguishing traits of *Fittonia* 'Red Star'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'Red Star'. Data was collected in Haaren, The Netherlands from 12 week old greenhouse grown plants in 8.5 cm. containers. The time of year was Fall and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Red Star' has not been tested under all possible conditions and phenotypic differences may be observed with variations in environmental, climatic, and cultural conditions, however, without any variance in genotype.

Botanical classification: *Fittonia verschaffeltii* 'Red Star'.
Use: Ornamental.
Parentage: 'Red Star' is a naturally occurring whole plant mutation of *Fittonia* 'Josan'.
Vigor: Moderate.
Growth rate: Moderate.
Growth habit: Broad spreading, upright.
Plant shape: Flattened globose.
Suitable container size: 8.5 cm. diameter container.
Height: Average 5.4 cm.
Width: Average 12.3 cm.

Hardiness: USDA Zone 10.
Propagation: Terminal cuttings.
Time to initiate roots: Approximately 21 days to produce roots on an initial cutting at 24° Centigrade.
Time to produce a rooted cutting: Approximately 35 days to produce a rooted cutting at 24° Centigrade.
Crop time: 12 weeks.
Root system: Fine and fibrous.
Stem:
*Branching habit.*—Moderately branching.
*Average number of lateral branches.*—2.
*Pinching.*—No.
*Lateral branch diameter.*—3 mm. in diameter, thickened at the nodes, 4 mm in diameter.
*Lateral branch length.*—1.7 cm in length.
*Lateral branch strength.*—Moderate.
*Lateral branch color.*—200C with tinges of 143D.
*Stem color.*—200C.
*Pubescence.*—Dense, length 1.7 mm, color N155A.
*Internode length.*—1.5 mm. between nodes.
*Internode color.*—143C to 143D.
*Shape.*—Rounded.
*Surface.*—Dull.
*Stem strength.*—Moderate to strong.
Foliage:
*Leaf arrangement.*—Opposite.
*Compound or single.*—Single.
*Leaf shape.*—Broad obovate to elliptic.
*Leaf apex.*—Broad apiculate.
*Leaf base.*—Attenuate.
*Leaf texture.*—Slightly glossy and slightly rugose with furrowed venation.
*Leaf length.*—Average 4.9 cm. in length.
*Leaf width.*—3.1 cm. in width.
*Quantity of leaves per lateral branch.*—Average 6.
*Pubescence.*—Short hairs on margins, 0.5 mm. in length, N155A.
*Leaf margin.*—Considerably wavy.
*Vein pattern.*—Pinnate.
*Young leaf color, (upper surface).*—143A to 143C, margins 139A.
*Young leaf color, (lower surface).*—138A.
*Mature leaf color, (upper surface).*—139A.
*Mature leaf color, (lower surface).*—138A.
*Vein color (upper surface).*—53B, margins 53B to 53C.
*Vein color (lower surface).*—144D.
*Leaf attachment.*—Petiolate.
*Petiole dimensions.*—Average 1 cm. in length, 2.5 mm. in diameter, 2 mm. in height.
*Petiole color (upper surface).*—178A.
*Petiole color (lower surface).*—146A.
*Durability of foliage to stress.*—High.
Flowers: Flowers have not been observed.
Disease and insect resistance: Plants of the new *Fittonia* have not been observed for disease or insect resistance.

It is claimed:

1. A new and distinct variety of *Fittonia* plant named 'Red Star' as described and illustrated.

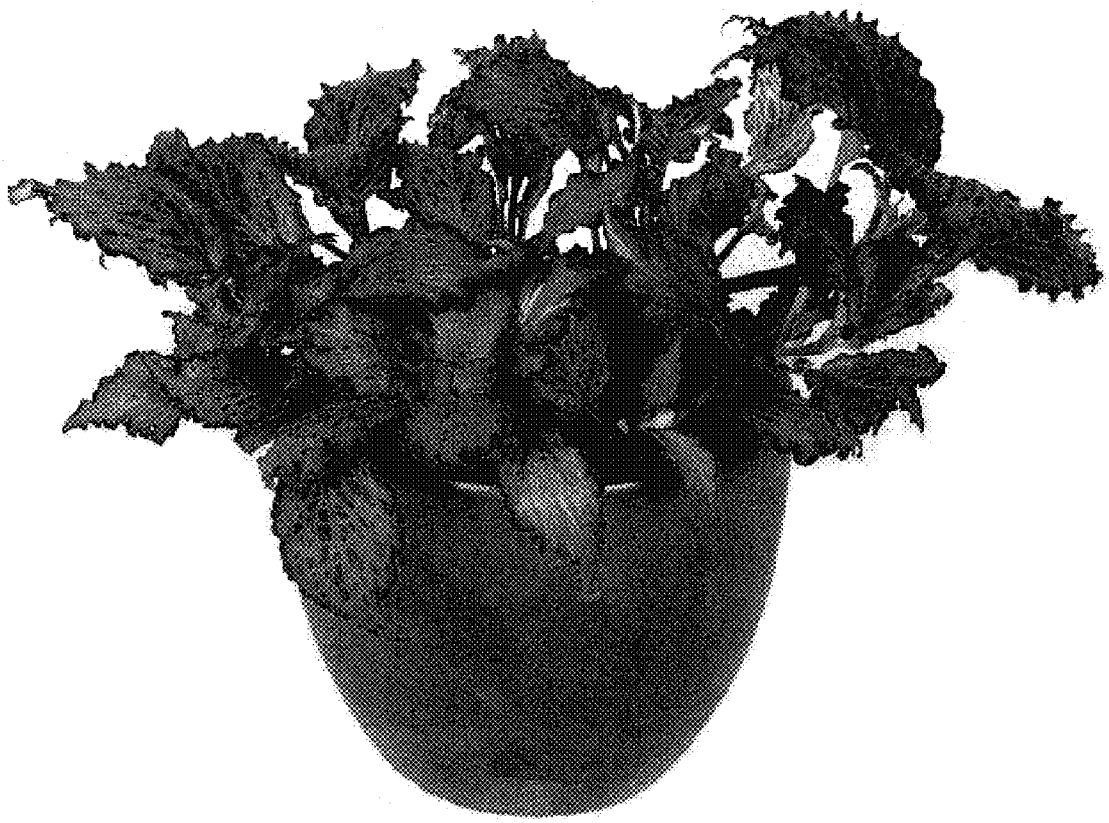

* * * * *